US011419817B2

(12) United States Patent
Barrett et al.

(10) Patent No.: US 11,419,817 B2
(45) Date of Patent: Aug. 23, 2022

(54) DRUG DELIVERY SYSTEM FOR THE DELIVERY OF ANTIVIRAL AGENTS

(71) Applicants: Merck Sharp & Dohme Corp., Rahway, NJ (US); Stephanie Elizabeth Barrett, Quakertown, PA (US); Marian E. Gindy, North Wales, PA (US); Li Li, North Wales, PA (US); Ryan S. Teller, Sierra Madre, CA (US); Seth P. Forster, Fort Washington, PA (US)

(72) Inventors: Stephanie Elizabeth Barrett, Quakertown, PA (US); Marian E. Gindy, North Wales, PA (US); Li Li, North Wales, PA (US); Ryan S. Teller, Sierra Madre, CA (US); Seth P. Forster, Fort Washington, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 252 days.

(21) Appl. No.: 16/603,692

(22) PCT Filed: Apr. 5, 2018

(86) PCT No.: PCT/US2018/026164
§ 371 (c)(1),
(2) Date: Oct. 8, 2019

(87) PCT Pub. No.: WO2018/191093
PCT Pub. Date: Oct. 18, 2018

(65) Prior Publication Data
US 2021/0093555 A1    Apr. 1, 2021

Related U.S. Application Data

(60) Provisional application No. 62/483,656, filed on Apr. 10, 2017.

(51) Int. Cl.
*A61K 9/00* (2006.01)
*A61K 31/52* (2006.01)

(52) U.S. Cl.
CPC ............ *A61K 9/0024* (2013.01); *A61K 31/52* (2013.01)

(58) Field of Classification Search
CPC .... A61K 9/0024; A61K 9/284; A61K 9/2853; A61K 9/2866; A61K 31/52; A61K 9/2072; A61P 31/18
See application file for complete search history.

(56) References Cited

U.S. PATENT DOCUMENTS

| | | |
|---|---|---|
| 4,148,871 A | 4/1979 | Pitt et al. |
| 2005/0215512 A1 | 9/2005 | Kohgo et al. |
| 2016/0339030 A1 | 11/2016 | Redfield et al. |

FOREIGN PATENT DOCUMENTS

| | | | |
|---|---|---|---|
| WO | 2016149561 A1 | 9/2016 | |
| WO | WO-2016149561 A1 * | 9/2016 | ........... A61K 31/513 |
| WO | WO2017196697 A1 | 11/2017 | |
| WO | WO2017222903 A1 | 12/2017 | |

OTHER PUBLICATIONS https://en.wikipedia.org/wiki/Modified-release_dosage retrieved Aug. 24, 2021. (Year: 2021).*
Hattori, S., et al., "Potent Activity of a Nucleoside Reverse Transcriptase Inhibitor", Antimicrobial Agents and Chemotherapy, 2009, pp. 3887-3893, vol. 53.
International Search Report and Written Opinion for PCT/US2018/026164, dated Jun. 21, 2018; 6 pages.
Stoddart, C.A., et al, "Oral Administration of the Nucleoside EFdA (4'-Ethynyl-2-Fluoro-2'-Deoxyadenosine) Provides Rapid Suppression of HIV Viremia in Humanized Mice and Favorable Pharmacokinetic Properties in Mice and the Rhesus Macaque", Antimicrobial Agents and Chemotherapy, 2015, pp. 4190-4198, vol. 59, No. 7.
Grosu, E., et al., "Study of the Drug Diffusion Through Polymeric Membranes", Rev.Chim. (Bucharest) 2018, pp. 783-789, 69, No. 4.

* cited by examiner

*Primary Examiner* — Blessing M Fubara
(74) *Attorney, Agent, or Firm* — Daniel Woods; John C. Todaro

(57) ABSTRACT

This invention relates to novel implant drug delivery systems for long-acting delivery of antiviral drugs. These compositions are useful for the treatment or prevention of human immunodeficiency virus (HIV) infection.

12 Claims, No Drawings

DRUG DELIVERY SYSTEM FOR THE DELIVERY OF ANTIVIRAL AGENTS

BACKGROUND OF THE INVENTION

The development of highly active antiretroviral therapy (HAART) in the mid 1990's transformed the clinical care of human immunodeficiency virus (HIV) type infection. HAART regimens have proven to be highly effective treatments, significantly decreasing HIV viral load in HIV-infected patients, thereby slowing the evolution of the illness and reducing HIV-related morbidity and mortality. Yet, the treatment success of HAART is directly related to adherence to the regimen by the patient. Unless appropriate levels of the antiretroviral drug combinations are maintained in the blood, viral mutations will develop, leading to therapy resistance and cross-resistances to molecules of the same therapeutic class, thus placing the long-term efficacy of treatments at risk. Various clinical studies have shown a decline in treatment effectiveness with relatively small lapses in adherence. A study by Musiime found that 81% of patients with more than 95% adherence demonstrated viral suppression, while only 50% of patients who were 80-90% adherent were successful. See, Musiime, S., et al., Adherence to Highly Active Antiretroviral Treatment in HIV-Infected Rwandan Women. *PLOS one* 2011, 6, (11), 1-6. Remarkably, only 6% of patients that were less than 70% adherent showed improvements in viral markers. Thus, low adherence is a leading cause of therapeutic failure in treatment of HIV-1 infection.

Nonetheless, adherence rates to the HAART regimens continue to be far from optimal. Various characteristics of HAART make adherence particularly difficult. Therapeutic regimens are complex, requiring multiple drugs to be taken daily, often at different times of the day, and many with strict requirements on food intake. Many HAART medications also have unpleasant side effects, including nausea, diarrhea, headache, and peripheral neuropathy. Social and psychological factors can also negatively impact adherence. Patients report that forgetfulness, lifestyle factors, including fear of being identified as HIV-positive, and therapy fatigue over life-long duration of treatment all contribute to adherence lapses.

New HIV treatment interventions aim to improve adherence by reducing the complexity of treatments, the frequency of the dosages, and/or the side effects of the medications. Long-acting injectable (LAI) drug formulations that permit less frequent dosing, on the order of a month or longer, are an increasingly attractive option to address adherence challenges. However, the majority of approved and investigational antiretroviral agents are not well suited for reformulation as long-acting injectable products. In large part, this is due to suboptimal physicochemical properties limiting their formulation as conventional drug suspensions, as well as insufficient antiviral potency resulting in high monthly dosing requirements. Even for cabotegravir or rilpivirine, two drugs being studied as long-acting injectible formulations, large injection volumes and multiple injections are required to achieve pharmacokinetic profiles supportive of monthly dosing. See, e.g., Spreen, W. R., et al., Long-acting injectable antiretrovirals for HIV treatment and prevention. *Current Opinion in Hiv and Aids* 2013, 8, (6), 565-571; Rajoli, R. K. R., et al., Physiologically Based Pharmacokinetic Modelling to Inform Development of Intramuscular Long-Acting Nanoformulations for HIV. *Clinical Pharmacokinetics* 2015, 54, (6), 639-650; Baert, L., et al., Development of a long-acting injectable formulation with nanoparticles of rilpivirine (TMC278) for HIV treatment. *European Journal of Pharmaceutics and Biopharmaceutics* 2009, 72, (3), 502-508; Van't Klooster, G., et al., Pharmacokinetics and Disposition of Rilpivirine (TMC278) Nanosuspension as a Long-Acting Injectable Antiretroviral Formulation. *Antimicrobial Agents and Chemotherapy* 2010, 54, (5), 2042-2050. Thus, novel formulation approaches capable of delivering extended-duration pharmacokinetic characteristics for molecules of diverse physicochemical properties at practical injection volumes and with a limited number of injections are highly desirable.

SUMMARY OF THE INVENTION

This invention relates to novel implant drug delivery systems for long-acting delivery of antiviral drugs. These compositions are useful for the treatment or prevention of human immunodeficiency virus (HIV) infection.

DETAILED DESCRIPTION OF THE INVENTION

This invention relates to novel implant drug delivery systems for long-acting delivery of antiviral drugs. The novel implant drug delivery systems comprise a polymer and an antiviral agent. These implant drug delivery systems are useful for the treatment or prevention of human immunodeficiency virus (HIV) infection. The invention further relates to methods of treating and preventing HIV infection with the novel implant drug delivery systems described herein.

The novel implant delivery systems of the invention comprise a biocompatible polymer encapsulating a pharmaceutical composition. The biocompatible polymer can be either a biocompatible nonerodible polymer or a biocompatible erodible polymer. The chemical properties of the polymer matrices are tuned to achieve a range of drug release characteristics, offering the opportunity to extend duration of dosing. In an embodiment of the invention, the novel implant delivery systems are compatible with molecules suitable for formulation as solid drug suspensions.

This invention relates to novel implant drug delivery systems for subcutaneous implantation comprising a biocompatible polymer and a pharmaceutical composition comprising 4'-ethynyl-2-fluoro-2'-deoxyadenosine, wherein said 4'-ethynyl-2-fluoro-2'-deoxyadenosine is continually released in vivo at a rate resulting in a plasma concentration between 0.01 ng/mL and 3000.0 ng/mL. In a specific embodiment, this invention relates to novel implant drug delivery systems for subcutaneous implantation comprising a biocompatible polymer and a pharmaceutical composition comprising 4'-ethynyl-2-fluoro-2'-deoxyadenosine, wherein said 4'-ethynyl-2-fluoro-2'-deoxyadenosine is continually released in vivo at a rate resulting in a plasma concentration between 0.01 ng/mL and 25.0 ng/mL. The novel implant drug delivery systems of the instant invention are implanted subcutaneously. These implant delivery systems are desired and useful for prophylaxis and/or treatment of HIV infection from both compliance and convenience standpoints.

As used herein, the term "biocompatible nonerodible polymer" refers to polymeric materials that are sufficiently resistant to degradation (both chemical and physical) in the presence of biological systems. Biocompatible nonerodible polymers are sufficiently resistant to chemical and/or physical destruction by the environment of use such that the polymer remains essentially intact throughout the release period. Nonerodible polymers remain intact in vivo for extended periods of time, typically months or years. Drug molecules encapsulated in the polymer are released over time via diffusion through channels and pores in a sustained manner. The release rate can be altered by modifying the percent drug loading, porosity of the polymer, structure of the implantable device, or hydrophobicity of the polymer, or by adding a hydrophobic coating to the exterior of the implantable device.

Accordingly, any polymer that cannot be absorbed by the body can be used to manufacture the implant drug delivery systems of the instant invention that comprise a biocompatible nonerodible polymer. Biocompatible nonerodible polymers of the instant invention include, but are not limited to, ethylene vinyl acetate copolymer (EVA), polyurethane, silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyamide, polysulphones, styrene acrylonitrile copolymers, crosslinked poly(ethylene oxide), poly(alkylenes), poly(vinyl imidazole), poly(esters), poly(ethylene terephthalate), polyphosphazenes, and chlorosulphonated polyolefines, and combinations thereof. In a class of the invention, the biocompatible nonerodible polymer is polyurethane. In a subclass of the invention, the biocompatible nonerodible polymer is selected from the group consisting of hydrophilic polyurethane and hydrophobic polyurethane. In a further subclass of the invention, the biocompatible nonerodible polymer is hydrophilic polyurethane. In a further subclass of the invention, the biocompatible nonerodible polymer is hydrophobic polyurethane.

As used herein, the term "biocompatible bioerodible polymer" refers to polymeric materials that include hydrolytically labile linkages which undergo cleavage at physiological conditions. The broken down products are non-toxic and either excreted in the urine or incorporated into the Krebs cycle and used for energy. The polymer is generally hydrophobic so that it retains its integrity for a suitable period of time when placed in an aqueous environment, such as the body of a mammal, and is stable enough to be stored for an extended period before use. Bioerodible polymers remain intact in vivo for extended periods of time, typically weeks, months or years. Drug molecules encapsulated in the polymer are released over time via diffusion through channels and pores in a sustained manner. The release rate can be altered by modifying the identity of the polymer (monomeric units, molecular weight, end group, etc.) thereby modifying the degradation kinetics, percent drug loading, porosity of the polymer, structure of the implantable device, or hydrophobicity of the polymer, or by adding a hydrophobic coating to the exterior of the implantable device.

Accordingly, any polymer that can be readily cleared or eliminated by the body can be used to manufacture the implant drug delivery systems of the instant invention that comprise a biocompatible bioerodible polymer. The term "polymer" can also include copolymers. Biocompatible bioerodible polymers of the instant invention include, but are not limited to, poly(lactic-co-glycolic acid) ("PLGA"), poly(DL-lactide) ("PLA"), poly(caprolactone) ("PCL"), poly(lactide-co-glycolide), poly(lactide), poly(glycolide) ("PLG"), poly(ε-caprolactone), poly(ortho esters), poly(dioxanone), poly(alkylcyanoacrylates) and combinations thereof. In a class of the invention, the biocompatible bioerodible polymer is selected from the group consisting of poly(DL-lactide) and poly(caprolactone).

In a class of the invention, the biocompatible bioerodible polymer is poly(lactic-co-glycolic acid) ("PLGA").

As used herein, the term "continually released" refers to the drug being released from the biocompatible polymer at continuous rates for extended periods of time.

In an embodiment of the invention, the biocompatible polymer contains an antiviral drug. In a class of the embodiment, the biocompatible polymer contains 4'-ethynyl-2-fluoro-2'-deoxyadenosine.

Optionally, the novel implant delivery systems of the instant invention can further comprise a radiopaque component. The radiopaque component will cause the implant to be X-ray visible. The radiopaque component can be any such element known in the art, such as barium sulfate, titanium dioxide, bismuth oxide, tantalum, tungsten or platinum. In a specific embodiment, the radiopaque component is barium sulfate.

The novel implant delivery systems of the invention comprise pharmaceutical compositions of antiviral agents. Suitable antiviral agents include anti-HIV agents. In an embodiment of the invention, the antiviral agent is administered as a monotherapy. In another embodiment of the invention, two or more antiviral agents are administered in combination.

An "anti-HIV agent" is any agent which is directly or indirectly effective in the inhibition of HIV reverse transcriptase or another enzyme required for HIV replication or infection, the or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. Suitable anti-viral agents for use in implant drug delivery systems described herein include, for example, those listed in Table A as follows:

TABLE A

Antiviral Agents for Preventing HIV infection or AIDS

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| Capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| doravirine | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| Lopinavir | PI |

TABLE A-continued

Antiviral Agents for Preventing HIV infection or AIDS

| Name | Type |
| --- | --- |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, Isentress ™ | InI |
| (S)-2-(3-chloro-4-fluorobenzyl)-8-ethyl-10-hydroxy-N,6-dimethyl-1,9-dioxo-1,2,6,7,8,9-hexahydropyrazino[1',2': 1,5]pyrrolo[2,3-d]pyridazine-4-carboxamide (MK-2048) | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyl oxypropyl (CMX-157) | nRTI |
| tipranavir, Aptivus ® | PI |
| Vicriviroc | EI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor.

Some of the drugs listed in the table can be used in a salt form; e.g., abacavir sulfate, delavirdine mesylate, indinavir sulfate, atazanavir sulfate, nelfinavir mesylate, saquinavir mesylate.

In certain embodiments the antiviral agents in the implant drug delivery systems described herein are employed in their conventional dosage ranges and regimens as reported in the art, including, for example, the dosages described in editions of the *Physicians' Desk Reference*, such as the 70th edition (2016) and earlier editions. In other embodiments, the antiviral agents in the implant drug delivery systems described herein are employed in lower than their conventional dosage ranges.

In an embodiment of the invention, the antiviral agent can be an entry inhibitor; fusion inhibitor; integrase inhibitor; protease inhibitor; nucleoside reverse transcriptase inhibitor; or non-nucleoside reverse transcriptase inhibitor. In a class of the invention, the antiviral agent is a nucleoside reverse transcription inhibitor.

In an embodiment of the invention, the antiviral agent is a nucleoside reverse transciptase inhibitor (NRTI). In a class of the invention, the NRTI is 4'-ethynyl-2-fluoro-2'-deoxyadenosine.

4'-ethynyl-2-fluoro-2'-deoxyadenosine is also known as EFdA, and has the following chemical structure:

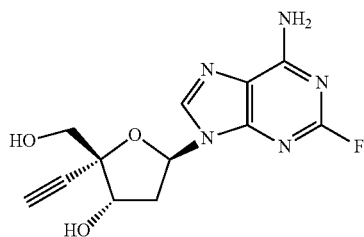 [SMILES: C#C[C@]1(CO)O[C@@H](n2cnc3c(N)nc(F)nc32)C[C@@H]1O]

Production of and the ability of 4'-ethynyl-2-fluoro-2'-deoxyadenosine to inhibit HIV reverse transcriptase are described in PCT International Application WO2005090349, published on Sep. 29, 2005, and US Patent Application Publication No. 2005/0215512, published on Sep. 29, 2005, both to Yamasa Corporation which are hereby incorporated by reference in their entirety.

The novel implant delivery systems of the invention comprise a biocompatible polymer that encapsulates the pharmaceutical composition. In an embodiment of the invention, the pharmaceutical composition comprises 4'-ethynyl-2-fluoro-2'-deoxyadenosine, a diluent and a lubricant. In an embodiment of the invention, the pharmaceutical composition is a tablet.

The term "tablet" as used herein is intended to encompass compressed pharmaceutical dosage formulations of all shapes and sizes.

The pharmaceutical compositions of the present invention may contain one or more additional formulation ingredients that may be selected from a wide variety of excipients known in the pharmaceutical formulation art. According to the desired properties of the compositions, any number of ingredients may be selected, alone or in combination, based upon their known uses in preparing tablet compositions. Such ingredients include, but are not limited to, diluents, binders, compression aids, disintegrants, lubricants, glidants, stabilizers (such as desiccating amorphous silica), preservatives and coatings.

In an embodiment of the invention, the diluents are selected from the group consisting of lactose, lactose anhydrous, lactose monohydrate, mannitol, sucrose, dextrose anhydrous, dextrose monohydrate, and mannitol. In a class of the embodiment, the diluent is lactose.

In an embodiment of the invention, the lubricant is magnesium stearate, stearic acid or sodium stearyl fumarate. In a class of the embodiment, the lubricant is magnesium stearate.

In an embodiment of the implant drug delivery system described herein, the antiviral agent is present in the tablet at about 0.10%-99% by weight of drug loading. In other embodiments, the antiviral agent is present in the tablet at about 60%-99% by weight, at about 80%-99% by weight or at about 90%-99% by weight of drug loading. In an example of the embodiment of the implant drug delivery system described herein, 4'-ethynyl-2-fluoro-2'-deoxyadenosine is present in the tablet at 99% by weight of drug loading. In another example of the embodiment of the implant drug delivery system described herein, 4'-ethynyl-2-fluoro-2'-deoxyadenosine is present in the tablet at 80% by weight of drug loading.

The implant drug delivery systems of the instant invention may be produced by compressing the drug with excipient to form a tablet, and then coating or containing single or multiple tablets within a polymer capsule. Methods for encapsulating therapeutic compounds within implantable polymeric capsules are known to those of skill in the art. One of skill in the art would be able to readily determine an appropriate method of preparing such an implant drug delivery system, depending on the shape, size, drug loading, and release kinetics desired for a particular type of patient or clinical application.

The size and shape of the implant drug delivery systems may be modified to achieve a desired overall dosage. The implant drug delivery systems of the instant invention are often about 0.5 cm to about 10 cm in length. In an embodiment of the invention, the implant drug delivery systems are about 1.5 cm to about 5 cm in length. In a class of the embodiment, the implant drug delivery systems are about 2 cm to about 5 cm in length. In a subclass of the embodiment, the implant drug delivery systems are about 2 cm to about 4 cm in length. The implant drug delivery systems of the instant invention are often about 0.5 mm to about 7 mm in diameter. In an embodiment of the invention, the implant drug delivery systems are about 1.5 mm to about 5 mm in diameter. In a class of the embodiment, the implant drug delivery systems are about 2 mm to about 5 mm in diameter. In a subclass of the embodiment, the implant drug delivery systems are about 2 mm to about 4 mm in diameter.

The implant drug delivery systems described herein are capable of releasing 4'-ethynyl-2-fluoro-2'-deoxyadenosine over a period of 21 days, 28 days, 31 days, 4 weeks, 6 weeks, 8 weeks, 12 weeks, one month, two months, three months, four months, five months, six months, seven months, eight months, nine months, ten months, eleven months, twelve months, eighteen months, twenty-four months or thirty-six months at an average rate of between 0.01-5 mg per day. In an embodiment of the invention, the 4'-ethynyl-2-fluoro-2'-deoxyadenosine is released at therapeutic concentrations for a duration from between three months and thirty-six months. In a class of the embodiment, the 4'-ethynyl-2-fluoro-2'-deoxyadenosine is released at therapeutic concentrations for a duration from between six months and twelve months.

The implant drug delivery systems described herein are capable of releasing 4'-ethynyl-2-fluoro-2'-deoxyadenosine resulting in a plasma concentration of between 0.01-10 ng/mL per day. In an embodiment of the invention, the implant drug delivery systems described herein are capable of releasing 4'-ethynyl-2-fluoro-2'-deoxyadenosine resulting in a plasma concentration of between 0.1-5.0 ng/mL per day. In a class of the embodiment, the implant drug delivery systems described herein are capable of releasing 4'-ethynyl-2-fluoro-2'-deoxyadenosine resulting in a plasma concentration of between 0.1-2 ng/mL per day. In a subclass of the embodiment, the implant drug delivery systems described herein are capable of releasing 4'-ethynyl-2-fluoro-2'-deoxyadenosine resulting in a plasma concentration of between 0.1-1.0 ng/mL per day.

The following examples are given for the purpose of illustrating the present invention and shall not be construed as being limitations on the scope of the invention.

Example 1

Preparation and In Vitro Release of Implant Drug Delivery Systems Containing 4'-ethynyl-2-fluoro-2'-deoxyadenosine The tablets were prepared by mixing the dry, micronized powder of the active compound, magnesium stearate at 1 wt %, and in certain cases lactose at 19 wt % using a Turbula T2F mixer. The 4'-ethynyl-2-fluoro-2'-deoxyadenosine blend was granulated, and then compressed into tablets. Tablets 3 mm in diameter, approximately 5.5 mm in length, and approximately 50 mg each were compressed at 10 kN, and then enclosed within a polymer capsule by dip-coating or spray-coating. For dip-coating, the tablets were dipped in a polymer solution of 10 wt % polymer in tetrahydrofuran and dried (Table 2 and 3). Both a hydrophilic and hydrophobic polyurethanes, as well as a 75:25 poly(D, L-lactide-co-glycolide) (PLGA) with lauryl ester end group capsule and an inherent viscosity of 0.4 dL/g (~0.5 wt % in chloroform at 30° C.) were used for dip-coating. The procedure was repeated until the desired capsule thickness was achieved. For spray-coating, a solution of 4 wt % hydrophilic polyurethane in tetrahydrofuran was applied to tablets that were being actively agitated with a vortex mixer (Table 4). The mass of the polymer capsule was comparable for the dip- and spray-coating methods. The capsule thickness was 0.1 mm by dip-coating, and 0.4 mm by spray-coating. Additionally, tablets 2 mm in diameter, approximately 8.5 mm in length, and approximately 25 mg each were compressed at 4 kN. For each implant, 3 tablets were sealed within an extruded hydrophilic polyurethane tube (Table 5). The tubing had an outer diameter of 2.5 mm, and internal diameter of 2.1 mm. The hydrophilic polyurethane polymer had an equilibrium swelling of 20 wt % in water.

The in vitro release rate of 4'-ethynyl-2-fluoro-2'-deoxyadenosine was determined by placing the implants into a glass vial containing phosphate buffered saline (PBS) at 37° C., and 50 rpm shaking in an Innova 42 incubator. The volume of PBS was sufficient to maintain sink conditions. Sink conditions are defined as the drug concentration maintained at or below ⅓ of the maximum solubility (drug concentration≤0.45 mg/mL in PBS at 37° C.). Samples were removed (0.5 mL) at selected time points, and centrifuged at 20,800×g for 8 min. The supernatant was removed (0.4 mL), diluted 4-fold, and vortexed. Samples were assayed by HPLC (Agilent 1100 series). Analysis of a 6 µL volume was performed at 240 nm with a Supelco Ascentis® Express C18 column (100×4.6 mm, 2.7 µm). The mobile phase was 0.1% $H_3PO_4$ and 50:50 ACN:MeOH (83:17 v/v) at a flow rate of 1.5 mL/min (40° C.).

To determine degradation of MK-8591 by HPLC, a 6 µL volume was injected onto an Agilent Zorbax SB-Aq column (150×4.6 mm, 3.5 µm). The mobile phase was 0.1% $H_3PO_4$ and 50:50 ACN:MeOH with a flow rate of 1.0 mL/min (40° C.). The mobile phase gradient is shown in the table below. All samples were calibrated to 0.5 mg/mL standard solutions of 4'-ethynyl-2-fluoro-2'-deoxyadenosine in 50:50 MeOH:$H_2O$.

TABLE 1

4'-ethynyl-2-fluoro-2'-deoxyadenosine chemical stability HPLC method details

| Time (min) | 0.1% $H_3PO_4$ (%) |
|---|---|
| 0.0 | 98 |
| 10.0 | 95 |
| 12.0 | 90 |
| 14.0 | 10 |
| 14.1 | 98 |
| 20.0 | 98 |

TABLE 2

4'-ethynyl-2-fluoro-2'-deoxyadenosine in vitro release from 80 and 99 wt % drug load (DL) tablets contained within a dip-coated polyurethane capsule; reported as a % release from total [avg. = average and std. dev. = standard deviation]

| | 99 wt % DL tablet and dip-coated hydrophilic polyurethane capsule | | 80 wt % DL tablet and dip-coated hydrophilic polyurethane capsule | | 80 wt % DL tablet and dip-coated hydrophobic polyurethane capsule | |
|---|---|---|---|---|---|---|
| Time (days) | Avg. (%) | Std. Dev. (%) | Avg. (%) | Std. Dev. (%) | Avg. (%) | Std. Dev. (%) |
| 7 | 11.9 | 0.6 | 19 | 3 | 0.7 | 0.1 |
| 14 | 22 | 2 | 33 | 2 | 1.4 | 0.1 |
| 21 | 34 | 4 | 42 | 3 | 2.1 | 0.1 |
| 28 | 39 | 5 | 57.4 | 0.4 | 3.1 | 0.3 |
| 35 | 45 | 5 | 67 | 1 | 3.9 | 0.5 |
| 43 | 59 | 8 | 86 | 2 | 5.5 | 0.6 |
| 49 | 65 | 10 | 93 | 2 | 6.2 | 0.7 |
| 56 | | | 102 | 3 | 7.2 | 0.8 |
| 70 | 85 | 14 | | | 9.0 | 0.9 |
| 76 | 91 | 13 | | | 10.1 | 0.9 |
| 84 | 96 | 12 | | | 11 | 1 |

TABLE 3

4'-ethynyl-2-fluoro-2'-deoxyadenosine in vitro release from 99 wt % DL tablets contained within a PLGA capsule; reported as a % release from total [avg. = average and std. dev. = standard deviation]

| | 99 wt % DL tablet and dip-coated PLGA capsule | |
|---|---|---|
| Time (days) | Avg. (%) | Std. Dev. (%) |
| 7 | 0.5 | 0.2 |
| 14 | 1.4 | 0.5 |
| 21 | 1.8 | 0.7 |
| 28 | 3.3 | 1.0 |
| 35 | 3.6 | 0.8 |
| 49 | 4.8 | 1.7 |
| 56 | 5.5 | 2.0 |
| 71 | 8.7 | 2.4 |
| 78 | 12 | 3 |
| 97 | 22 | 4 |
| 104 | 23 | 4 |
| 111 | 26 | 5 |
| 118 | 29 | 4 |
| 125 | 31 | 4 |
| 132 | 33 | 5 |
| 152 | 40 | 7 |
| 162 | 43 | 7 |
| 169 | 46 | 7 |
| 175 | 48 | 7 |
| 182 | 52 | 7 |
| 189 | 53 | 7 |
| 197 | 56 | 7 |
| 205 | 59 | 7 |
| 211 | 62 | 8 |
| 219 | 68 | 8 |
| 240 | 87 | 10 |

TABLE 4

4'-ethynyl-2-fluoro-2'-deoxyadenosine in vitro release from 99 wt % DL tablets contained within a spray-coated polyurethane capsule; reported as a % release from total [avg. = average and std. dev. = standard deviation]

| | 99 wt % DL tablet and spray-coated hydrophilic polyurethane capsule | |
|---|---|---|
| Time (days) | Avg. (%) | Std. Dev. (%) |
| 8 | 32 | 3 |
| 14 | 57 | 4 |
| 28 | 92 | 5 |
| 35 | 95 | 6 |

TABLE 5

4'-ethynyl-2-fluoro-2'-deoxyadenosine in vitro release from 99 wt % DL tablets contained within an extruded polyurethane capsule; reported as a % release from total [avg. = average and std. dev. = standard deviation]

| | 99 wt % DL tablet and hydrophilic polyurethane tube | |
|---|---|---|
| Time (days) | Avg. (%) | Std. Dev. (%) |
| 3 | 1.4 | 0.6 |
| 7 | 5 | 2 |
| 14 | 13 | 4 |
| 31 | 39 | 5 |
| 41 | 54 | 7 |
| 48 | 66 | 5 |
| 55 | 73 | 5 |
| 61 | 82 | 5 |
| 70 | 94 | 5 |
| 77 | 98 | 4 |
| 84 | 103 | 3 |

TABLE 6

4'-ethynyl-2-fluoro-2'-deoxyadenosine in vitro release rates from 80 and 99 wt % DL tablets contained within polymer capsules

| Sample | Release rate (%/day) |
|---|---|
| 99 wt % DL and dip-coated hydrophilic polyurethane capsule | 1.1 |
| 80 wt % DL and dip-coated hydrophilic polyurethane capsule | 1.7 |
| 80 wt % DL and dip-coated hydrophobic polyurethane capsule | 0.14 |
| 99 wt % DL and dip-coated PLGA capsule | 0.34 |
| 99 wt % DL and spray-coated hydrophilic polyurethane capsule | 3.4 |
| 99 wt % DL and hydrophilic polyurethane tube | 1.4 |

Example 2

Preparation and In Vivo Release of Implant Drug Delivery Systems Containing 4'-ethynyl-2-fluoro-2'-deoxyadenosine The tablets were prepared by mixing the dry, micronized powder of the active compound, and magnesium stearate at 1 wt % using a Turbula T2F mixer. The 4'-ethynyl-2-fluoro-2'-deoxyadenosine blend was granulated, and then compressed into tablets. Tablets 2 mm in diameter, approximately 8.5 mm in length, and approximately 25 mg each were compressed at 4 kN. For each implant, 3 tablets were sealed within an extruded hydrophilic polyurethane tube. The tubing had an outer diameter of 2.5 mm, and internal diameter of 2.1 mm. The hydrophilic polyurethane polymer had an equilibrium swelling of 20 wt % in water.

All animal studies were conducted following protocols in accordance with the Institutional Animal Care and Use Committee (IACUC) at NIRC and Merck & Co., Inc., Kenilworth, N.J., U.S.A. which adhere to the regulations outlined in the USDA Animal Welfare Act. For each implantation, a Wistar Han rat was anesthetized using isoflurane to effect prior to subcutaneous dose administrations. The solid formulation was placed in the scapular region via a scalpel incision followed by subcutaneous placement. Three animals were used. Animals were monitored until recovered. At indicated time points, samples of blood were obtained from anesthetized animals (using isoflurane) and processed to plasma for determination of 4'-ethynyl-2-fluoro-2'-deoxyadenosine levels.

TABLE 7

4'-ethynyl-2-fluoro-2'-deoxyadenosine concentration in blood plasma from 99 wt % DL tablets contained within an extruded polyurethane capsule [avg. = average and std. dev. = standard deviation]

| | 99 wt % DL tablet and hydrophilic polyurethane tube | |
|---|---|---|
| Time (days) | Avg. (nM) | Std. Dev. (nM) |
| 0.041666667 | 61 | 102 |
| 0.083333333 | 29 | 30 |
| 0.166666667 | 50 | 78 |
| 1 | 14 | 12 |
| 2 | 67 | 19 |
| 4 | 103 | 27 |
| 9 | 116 | 25 |
| 11 | 161 | 33 |
| 16 | 165 | 58 |
| 18 | 187 | 53 |
| 23 | 213 | 71 |
| 25 | 169 | 36 |
| 30 | 193 | 53 |
| 32 | 215 | 101 |
| 37 | 250 | 158 |
| 39 | 170 | 51 |
| 44 | 180 | 38 |
| 46 | 199 | 34 |
| 51 | 188 | 73 |
| 58 | 203 | 52 |
| 65 | 225 | 67 |
| 72 | 225 | 67 |
| 79 | 173 | 23 |

What is claimed is:

1. An implant drug delivery system for subcutaneous implantation consisting essentially of one or more polyurethane coated tablets in the form of a capsule or tube, wherein the one or more tablets consist essentially of 4'-ethynyl-2-fluoro-2'-deoxyadenosine, and optionally a diluent and/or a lubricant, wherein said 4'-ethynyl-2-fluoro-2'-deoxyadenosine is continually released in vivo at a rate resulting in a plasma concentration between 0.1 ng/mL and 25.0 ng/mL.

2. The pharmaceutical composition of claim 1 wherein the optional diluent is lactose and the optional lubricant is magnesium stearate.

3. The implant drug delivery system of claim 1 wherein the plasma concentration is between 0.1 ng/mL and 5.0 ng/mL.

4. The implant drug delivery system of claim 3 wherein the plasma concentration is between 0.1 ng/mL and 1.0 ng/mL.

5. The polyurethane of claim 1 selected from the group consisting of hydrophilic polyurethane and hydrophobic polyurethane.

6. The polyurethane of claim 1 which is hydrophilic polyurethane.

7. The implant drug delivery system of claim 1 wherein the 4'-ethynyl-2-fluoro-2'-deoxyadenosine is released at therapeutic concentrations for a duration from between three months and thirty-six months.

8. The implant drug delivery system of claim 1 wherein the 4'-ethynyl-2-fluoro-2'-deoxyadenosine is released at therapeutic concentrations for a duration from between six months and twelve months.

9. A method of treating HIV infection with an implant drug delivery system according to claim 1 comprising implanting the implant drug delivery system of claim 1 in a patient in need thereof.

10. A method of preventing HIV infection with an implant drug delivery system according to claim 1 comprising implanting the implant drug delivery system of claim 1 in a patient in need thereof.

11. The implant drug delivery system of claim 1 wherein the implantable device is 2 mm to 6 mm in diameter and 2 cm to 5 cm in length.

12. The implant drug delivery system of claim 11 wherein one or more implants can be used to achieve the desired therapeutic dose for durations up to 2 years.

* * * * *

UNITED STATES PATENT AND TRADEMARK OFFICE
CERTIFICATE OF CORRECTION

Page 1 of 1

PATENT NO. : 11,419,817 B2
APPLICATION NO. : 16/603692
DATED : August 23, 2022
INVENTOR(S) : Barrett et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 266 days.

Signed and Sealed this
Eleventh Day of February, 2025

Coke Morgan Stewart
*Acting Director of the United States Patent and Trademark Office*